(12) United States Patent
Bates et al.

(10) Patent No.: US 7,700,728 B2
(45) Date of Patent: Apr. 20, 2010

(54) USE OF CHIMERIC RECEPTORS IN A SCREENING ASSAY FOR IDENTIFYING AGONISTS AND ANTAGONISTS OF CELL RECEPTORS

(75) Inventors: Elizabeth Esther Mary Bates, Lyons (FR); Estelle Merck, Prilly (CH); Odette de Bouteiller, Rillieux la pape (FR); Christophe Caux, Bressolles (FR)

(73) Assignee: Schering Corporation, Kenilworth, NJ (US)

( * ) Notice: Subject to any disclaimer, the term of this patent is extended or adjusted under 35 U.S.C. 154(b) by 401 days.

(21) Appl. No.: 11/388,884

(22) Filed: Mar. 24, 2006
(Under 37 CFR 1.47)

(65) Prior Publication Data
US 2007/0072202 A1    Mar. 29, 2007

Related U.S. Application Data

(60) Provisional application No. 60/664,904, filed on Mar. 24, 2005.

(51) Int. Cl.
*C07K 14/00*    (2006.01)
*A61K 38/16*    (2006.01)

(52) U.S. Cl. .......................................... 530/350; 514/12
(58) Field of Classification Search ....................... None
See application file for complete search history.

(56) References Cited

U.S. PATENT DOCUMENTS

| 2003/0022302 A1 | 1/2003 | Lewis et al. |
| 2003/0044429 A1 | 3/2003 | Aderem et al. |
| 2003/0104523 A1 | 6/2003 | Bauer et al. |
| 2003/0166001 A1 | 9/2003 | Lipford |
| 2004/0014779 A1 | 1/2004 | Gorden et al. |
| 2004/0022777 A1 | 2/2004 | Kolb et al. |
| 2004/0132079 A1 | 7/2004 | Gupta et al. |
| 2004/0197865 A1 | 10/2004 | Gupta et al. |

FOREIGN PATENT DOCUMENTS

| WO | WO 98/50547 | 11/1998 |
| WO | WO 01/90151 | 11/2001 |

*Primary Examiner*—Ruixiang Li

(57) ABSTRACT

The present invention provides novel materials and screening methods for identifying agonists and antagonists of cell receptors. Methods are disclosed for identifying agonists and antagonists using chimeric receptors comprising the extracellular ligand-binding domain of a first receptor fused with the transmembrane and intracellular domains of a second receptor containing an intracellular immunoreceptor tyrosine-based activation motif (ITAM).

9 Claims, No Drawings

USE OF CHIMERIC RECEPTORS IN A SCREENING ASSAY FOR IDENTIFYING AGONISTS AND ANTAGONISTS OF CELL RECEPTORS

CROSS-REFERENCE TO RELATED APPLICATIONS

This application claims priority benefit of U.S. provisional application No. 60/664,904, filed Mar. 24, 2005, which is incorporated by reference in its entirety.

FIELD OF THE INVENTION

The present invention relates to the field of screening methods for identifying compounds that act as agonists or antagonists of cellular receptors.

BACKGROUND OF THE INVENTION

Toll-like receptors (TLRs) are a family of at least ten highly conserved type-I transmembrane proteins (TLR1-TLR10) that are responsible for initiation of innate immune responses in vertebrates. They recognize a variety of pathogen-associated molecular patterns (PAMPs) from bacteria, viruses and fungi and act as a first line of defense against invading pathogens. Engagement of TLRs with their ligands leads to the production of various pro-inflammatory cytokines, chemokines, and effector molecules, depending on the cell type that is activated.

TLRs are characterized by an extracellular amino-terminal leucine-rich repeat (LRR) domain and a carboxy-terminal intracellular tail containing a conserved region called the Toll/interleukin-1 receptor (TIR) homology domain. The extracellular domain contains a varying number of LRR domains, which are presumably involved in ligand binding but may also be necessary for TLR dimerization.

PAMP ligands for most of the TLRs have been identified and include lipopolysaccharide (LPS) (recognized by TLR4), bacterial lipoproteins and lipoteichoic acid (recognized by TLR2), double stranded RNA (recognized by TLR3), flagellin (recognized by TLR5), single stranded viral RNA (recognized by TLR7 and TLR8), and viral and bacterial unmethylated CpG DNA (recognized by TLR9). In addition, host-derived ligands for several TLRs have been identified and include heat shock proteins (recognized by TLR4), chromatin-IgG complexes (recognized by TLR9), and endogenous mRNA (recognized by TLR3). No direct ligands have been identified for TLR 1 and TLR 6, but they appear to function as cofactors for TLR2.

Based on their ligands, TLRs 1, 2, 5 and 6 appear to specialize in recognition of products unique to bacteria and not made by the host. Their detection, therefore, affords a straight-forward self/non-self recognition. TLRs 3, 7, 8 and 9, on the other hand, specialize in viral detection and recognize nucleic acids, which are not unique to the microbial kingdom. In this case, self/non-self recognition is mediated not so much by the molecular nature of the ligands as by their accessibility to the TLRs. These TLRs are localized to intracellular compartments and detect viral nucleic acids in late endosomes-lysosomes. Because the host's nucleic acids are not normally accessible in these compartments, they do not trigger TLR-mediated signal transduction.

Once engaged, most TLRs initiate a signal transduction cascade leading to activation of NFκB via the adapter protein myeloid differentiation primary response gene 88 (MyD88) and recruitment of the IL-1 receptor associated kinase (IRAK). Phosphorylation of IRAK then leads to recruitment of TNF-receptor associated factor 6 (TRAF6), which then results in the phosphorylation of the NFκB inhibitor I-κB. As a result, NFκB enters the cell nucleus and initiates transcription of genes whose promoters contain NFκB binding sites, such as cytokines. TLR3, on the other hand, utilizes a MyD88-independent pathway to recruit TRIF to activate NFκB and IRF3, resulting in IFN-β production.

Various assays have been developed for identifying agonists and antagonists of TLRs (e.g., U.S. Patent Application publication Nos. 2004/0197865, 2004/0132079, 2004/022777, 2004/0014779, 2003/0166001, 2003/0104523, 2003/0044429, 2003/0022302). These assays, however, generally depend on the detection of delayed downstream events, such as cytokine production or reporter induction. Such delay in detection increases the likelihood that any toxicity associated with the test compound, the solvent, or the extracellular milieu will adversely affect the assay. As a result, there is an immediate need for a sensitive screening assay that allows detection of an immediate signal mediated by TLR engagement and materials for performing such an assay.

SUMMARY OF THE INVENTION

The present invention fills the foregoing need by providing such screening assays and materials. The invention provides novel chimeric receptors comprising the extracellular ligand-binding domain of a TLR fused with the transmembrane and intracellular domains of a receptor comprising an intracellular immunoreceptor tyrosine-based activation motif (ITAM). The invention also provides recombinant nucleic acids encoding such chimeric receptors, and recombinant vectors and host cells comprising such nucleic acids. The chimeric receptors can be expressed in mammalian cells where they display active ligand binding and trigger immediate calcium mobilization (i.e., flux) upon receptor activation. The invention further provides assay methods for the identification of agonists and antagonists of TLRs that may be useful in the prevention, treatment and management of diseases and conditions mediated by or influenced by TLR signaling.

Accordingly, one aspect of the present invention is directed to a chimeric receptor comprising the extracellular domain of a TLR and the transmembrane and intracellular domains of a receptor comprising an intracellular ITAM. In some embodiments, the chimeric receptor comprises the extracellular domain of TLR3 and the transmembrane and intracellular domains of CD32a. One such chimeric receptor comprises the mature amino acid sequence set forth in SEQ ID NO: 2. In other embodiments, the chimeric receptor comprises the extracellular domain of TLR2 and the transmembrane and intracellular domains of CD32a. One such chimeric receptor comprises the mature amino acid sequence set forth in SEQ ID NO: 4. In further embodiments, the chimeric receptors lack their associated signal peptides.

Another aspect of the present invention is directed to an isolated nucleic acid sequence encoding a chimeric receptor comprising the extracellular domain of a TLR and the transmembrane and intracellular domains of a receptor comprising an intracellular ITAM. In some embodiments, the nucleic acid sequence encodes a chimeric receptor comprising the extracellular domain of TLR3 and the transmembrane and intracellular domains of CD32a. One such nucleic acid sequence comprises the nucleotide sequence set forth in SEQ ID NO: 1. In other embodiments, the nucleotide sequence encodes a chimeric receptor comprising the extracellular domain of TLR2 and the transmembrane and intracellular domains of CD32a. One such nucleic acid sequence comprises the nucleotide sequence set forth in SEQ ID NO: 3.

Another aspect of the present invention is directed to a recombinant vector comprising a nucleic acid sequence encoding a chimeric receptor comprising the extracellular domain of a TLR and the transmembrane and intracellular domains of a receptor comprising an intracellular ITAM. Preferably, the recombinant vector is an expression vector in which the nucleic acid sequence is operably linked to a genetic control element capable of directing expression of the nucleic acid sequence in a host cell.

Another aspect of the present invention is directed to a host cell comprising a recombinant vector comprising a nucleic acid sequence encoding a chimeric receptor comprising the extracellular domain of a TLR and the transmembrane and intracellular domains of a receptor comprising an intracellular ITAM. The host cell can be prokaryotic or eukaryotic, but is preferably eukaryotic. Preferably, the host cell is a eukaryotic cell capable of displaying calcium mobilization. In one embodiment, the host cell is transiently transfected with a recombinant vector capable of directing expression of the chimeric receptor comprising the extracellular domain of a TLR and the transmembrane and intracellular domains of a receptor comprising an intracellular ITAM. In another embodiment, the host cell is stably transfected with the recombinant vector.

Another aspect of the present invention is directed to a method for producing a chimeric receptor comprising the extracellular domain of a TLR and the transmembrane and intracellular domains of a receptor comprising an intracellular ITAM comprising culturing a host cell comprising a recombinant vector comprising a nucleic acid molecule sequence encoding a chimeric receptor comprising the extracellular domain of a TLR and the transmembrane and intracellular domains of a receptor comprising an ITAM operably linked to a promoter sequence under conditions in which the nucleic acid sequence is expressed and the chimeric receptor comprising the extracellular domain of a TLR and the transmembrane and intracellular domains of a receptor comprising an intracellular ITAM is produced. In one embodiment, the host cell is a transiently transfected eukaryotic cell. In another embodiment, the host cell is a stably transfected eukaryotic cell. In a preferred embodiment, the host cell expresses the signaling molecules required for calcium mobilization.

Another aspect of the present invention is directed to a method for identifying a TLR agonist comprising: (a) providing a host cell capable of displaying calcium mobilization comprising a recombinant vector comprising a nucleic acid sequence encoding a chimeric receptor comprising the extracellular domain of a TLR and the transmembrane and intracellular domains of a receptor comprising an intracellular ITAM operably linked to a gene expression sequence; (b) culturing the host cell under conditions in which the nucleic acid sequence is expressed and the chimeric receptor is produced; (c) contacting the host cell with a candidate agent to be tested for TLR agonistic activity; and (d) measuring the level of calcium mobilization, whereby a TLR agonist is identified by measurement of an increased level of calcium mobilization compared to the level produced in the absence of such agonist. In some embodiments, one or more accessory molecules are co-expressed in the host cell for optimal cell surface expression and/or optimal recognition of ligands by the chimeric receptor. In one embodiment, the accessory molecule is one or more additional chimeric TLR receptors. In another embodiment, the accessory molecule is one or more non-TLR molecules.

Another aspect of the present invention is directed to a method for identifying a TLR antagonist comprising: (a) providing a host cell capable of displaying calcium mobilization comprising a recombinant vector comprising a nucleic acid sequence encoding a chimeric receptor comprising the extracellular domain of a TLR and the transmembrane and intracellular domains of a receptor comprising an intracellular ITAM operably linked to a gene expression sequence; (b) culturing the host cell under conditions in which the nucleic acid sequence is expressed and the chimeric receptor is produced; (c) contacting the host cell with a candidate agent to be tested for TLR antagonistic activity in the presence of a known TLR agonist; and (d) measuring the level of calcium mobilization, whereby a TLR antagonist is identified in the sample by measurement of a decreased level of calcium mobilization compared to the level produced in the presence of the known agonist alone. In some embodiments, the known TLR agonist is a natural ligand. In other embodiments, the known TLR agonist is a synthetic ligand.

Another aspect of the present invention is directed to a method for identifying a domain or residue critical for TLR/ligand or TLR/accessory interaction or TLR dimerization comprising: (a) providing a host cell capable of displaying calcium mobilization comprising a recombinant vector comprising a nucleic acid sequence encoding a chimeric receptor comprising the extracellular domain of a TLR and the transmembrane and intracellular domains of a receptor comprising an intracellular ITAM operably linked to a gene expression sequence, wherein the extracellular domain of the TLR comprises a modification of a domain or residue relative to an unmodified TLR; (b) culturing the host cell under conditions in which the nucleic acid sequence is expressed and the modified chimeric receptor is produced; (c) contacting the host cell with a known TLR agonist; and (d) measuring the level of calcium mobilization, whereby a change in the level of calcium mobilization compared to the level produced using a chimeric receptor comprising an unmodified extracellular domain of TLR is indicative of the criticality of the domain or residue on one or more of the interactions. In some embodiments, the modification is introduced by mutagenesis of the nucleic acid sequence encoding the extracellular domain of the TLR. In other embodiments, the modification is introduced post-translationally.

Another aspect of the present invention is directed to a method for identifying a receptor agonist comprising: (a) providing a host cell capable of displaying calcium mobilization comprising a recombinant expression vector comprising a nucleic acid sequence encoding a chimeric receptor comprising the extracellular domain of a first receptor and the transmembrane and intracellular domains of a second receptor comprising an intracellular ITAM operably linked to a gene expression sequence; (b) culturing the host cell under conditions in which the nucleic acid sequence is expressed and the chimeric receptor is produced; (c) contacting the host cell with a candidate agent to be tested for receptor agonistic activity; and (d) measuring the level of calcium mobilization, whereby a receptor agonist is identified by measurement of an increased level of calcium mobilization compared to the level produced in the absence of such agonist.

Another aspect of the present invention is directed to a method for identifying a receptor antagonist (a) providing a host cell capable of displaying calcium mobilization comprising a recombinant vector comprising a nucleic acid sequence encoding a chimeric receptor comprising the extracellular domain of a first receptor and the transmembrane and intracellular domains of a second receptor comprising an intracellular ITAM operably linked to a gene expression sequence;

(b) culturing the host cell under conditions in which the nucleic acid sequence is expressed and the chimeric receptor is produced; (c) contacting the host cell with a candidate agent to be tested for receptor antagonistic activity in the presence of a known agonist of said receptor; and (d) measuring the level of calcium mobilization, whereby a receptor antagonist is identified in the sample by measurement of a decreased level of calcium mobilization compared to the level produced in the presence of the known agonist alone.

DETAILED DESCRIPTION OF THE INVENTION

The present invention provides novel materials and methods useful for identifying TLR agonists and antagonists. The present invention is based on novel chimeric receptors comprising the extracellular domain of a TLR and the transmembrane and intracellular domains of a receptor comprising an intracellular ITAM. Engagement of the TLR portion of the chimeric receptor with a ligand results in dimerization of the chimeric receptor, thereby activating the intracellular ITAM domains and triggering immediate calcium mobilization. Such a calcium mobilization-based assay is distinct over assays that rely on either cytokine production or reporter induction, both of which suffer from an increased likelihood of cytotoxicity.

The materials and methods of the present invention utilize routine techniques in the field of molecular biology. Basic texts disclosing general molecular biology methods include Sambrook et al., *Molecular Cloning, A Laboratory Manual* (3d ed. 2001) and Ausubel et al., *Current Protocols in Molecular Biology* (1994).

To aid in the understanding of the invention, the following non-limiting definitions are provided:

The term "agonist" refers to a compound that can combine with a receptor to produce or increase a cellular activity. An agonist may be a ligand that directly binds to the receptor. Alternatively, an agonist may combine with a receptor indirectly by, for example, (a) forming a complex with another molecule that directly binds to the receptor, or (b) otherwise results in the modification of another compound so that the other compound directly binds to the receptor. An agonist may include a natural ligand.

The term "activate" and variations thereof refer to any measurable increase in cellular activity.

The term "antagonist" refers to a compound that can combine with a receptor to inhibit or reduce a cellular activity. An antagonist may be a ligand that directly binds to the receptor. Alternatively, an antagonist may combine with a receptor indirectly by, for example, (a) forming a complex with another molecule that directly binds to the receptor, or (b) otherwise results in the modification of another compound so that the other compound directly binds to the receptor.

The term "cellular activity" refers to a biological activity (e.g., cytokine production).

The term "wild-type" refers to a nucleic acid or protein that has the characteristics of that nucleic acid or protein when isolated from a naturally occurring source. A wild-type nucleic acid or protein is that which is most frequently observed in a population and is thus arbitrarily designated the "normal" or "wild-type" form of that molecule. In contrast, the term "modified" or "mutant" refers to a nucleic acid or protein that displays modifications in sequence and/or functional properties (i.e., altered characteristics) when compared to the wild-type nucleic acid or protein.

The term "transfection" refers to the uptake of DNA by a cell. A cell has been "transfected" when exogenous (i.e., foreign) DNA has been introduced inside the cell membrane. Transfection can be either transient (i.e., the introduced DNA remains extrachromosomal and is diluted out during cell division) or stable (i.e., the introduced DNA integrates into the cell genome or is maintained as a stable episomal element).

The term "co-transfection" refers to the simultaneous or sequential transfection of two or more nucleic acids into a cell.

The terms "promoter element" or "promoter" refer to a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences.

The terms "in operable combination", "in operable order" or "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The terms "selectable marker" or "selectable gene product" refer to the use of a nucleic acid sequence which encodes an enzymatic activity that confers resistance to an antibiotic or drug upon the cell in which the selectable marker is expressed. Selectable markers may be "positive"; positive selectable markers typically are dominant selectable markers, i.e., genes which encode an enzymatic activity that can be detected in a living cell or cell line. Selectable markers may also be "negative"; negative selectable markers encode an enzymatic activity (e.g., HSV thymidine kinase) whose expression is cytotoxic to the cell when grown in an appropriate selective medium (e.g., gancyclovir).

The term "vector" refers to a nucleic acid assembly capable of transferring gene sequences to target cells (e.g., viral vectors, non-viral vectors, particulate carriers, and liposomes). The term "expression vector" refers to a nucleic acid assembly containing a promoter that is capable of directing the expression of a sequence or gene of interest in a cell. Vectors typically contain nucleic acid sequences encoding selectable markers for selection of cells that have been transfected by the vector. Generally, the terms "vector construct," "expression vector," and "gene transfer vector," refer to any nucleic acid construct capable of directing the expression of a gene of interest and which can transfer gene sequences to target cells. Thus, the term includes cloning and expression vehicles, as well as viral vectors.

The term "reporter gene" refers to a nucleotide sequence included in an expression vector that confers a detectable phenotype. For example, the reporter gene may cause expression of a "reporter molecule", which confers a detectable phenotype on a cell.

The terms "agent" or "compound" describe any molecule, e.g. protein or pharmaceutical, that is screened for the capability of acting as an agonist or antagonist of a receptor or as an improved agonist or antagonist of a receptor.

The terms "treating" or "treatment" of a disease refer to executing a protocol, which may include administering one or more drugs to a patient (human or otherwise), in an effort to alleviate signs or symptoms of the disease. Thus, "treating" or "treatment" does not require complete alleviation of signs or symptoms, does not require a cure, and specifically includes protocols which have only marginal effect on the patient.

The present invention provides a chimeric receptor comprising the extracellular domain of a TLR and the transmembrane and intracellular domains of a receptor comprising an intracellular ITAM. ITAM consensus sequences (e.g., (E/D)-X-X- Y-X-X-(L/I)-$X_{6-8}$-Y-X-X-(L/I)) (SEQ ID NO: 11, wherein $X_{6-8}$ is $X_7$; SEQ ID NO: 12, wherein $X_{6-8}$ is $X_7$; and SEQ ID NO: 13, wherein $X_{6-8}$ is $X_8$) are present in the cytoplasmic domains of several molecules, including CD3, Igα/β, DAP 12, and CD32a (also referred to as FcγRIIA). The transmembrane and intracellular domains of any of these molecules (as well as other ITAM-containing molecules) can be combined with the extracellular domain of any TLR to produce a chimeric receptor of the present invention. For example, a chimeric receptor can comprise the extracellular domain of TLR3 and the transmembrane and intracellular domains of CD32a. One such chimeric receptor comprises the mature amino acid sequence set forth in SEQ ID NO: 2. A chimeric receptor can also comprise the extracellular domain of TLR2 and the transmembrane and intracellular domains of CD32a. One such chimeric receptor comprises the mature amino acid sequence set forth in SEQ ID NO: 4.

When expressed in cells, the chimeric receptors will typically lack their associated signal peptides. For example, a chimeric receptor comprising the extracellular domain of TLR3 and the transmembrane and intracellular domains of a receptor comprising an intracellular ITAM can comprise the amino acid sequence set forth in SEQ ID NO: 2 lacking the first 23-27 amino acids. Similarly, a chimeric receptor comprising the extracellular domain of TLR2 and the transmembrane and intracellular domains of a receptor comprising an intracellular ITAM can comprise the amino acid sequence set forth in SEQ ID NO: 4 lacking the first 18-20 amino acids. Various predictive methods exist for determining the amino acid sequences of mature secretory proteins lacking their signal peptides, including weight matrix algorithms and neural networking (Chou, *Protein Engineering* 14:75 (2001), which can then be verified by experimental methods, such as, e.g., N-terminal sequencing of the purified mature TLR proteins.

The chimeric receptor is produced by expression of a recombinant nucleic acid molecule comprising a nucleic acid encoding the extracellular domain of a TLR fused in frame to a nucleic acid encoding the transmembrane and intracellular domains of a receptor comprising an intracellular ITAM. For example, a recombinant nucleic acid molecule can comprise a nucleic acid sequence encoding the extracellular domain of human TLR3 fused in frame to a nucleic acid sequence encoding the transmembrane and intracellular domains of human CD32a. One such recombinant nucleic acid molecule comprises the nucleotide sequence set forth in SEQ ID NO: 1. A recombinant nucleic acid molecule can also comprise a nucleic acid sequence encoding the extracellular domain of human TLR2 fused in frame to a nucleic acid sequence encoding the transmembrane and intracellular domains of human CD32a. One such recombinant nucleic acid molecule comprises the nucleotide sequence set forth in SEQ ID NO: 3. Due to the degeneracy of the genetic code, however, many different nucleotide sequences can encode the chimeric receptors of SEQ ID NOs:2 and 4. The codons can be selected for optimal expression in prokaryotic or eukaryotic systems.

The nucleic acid sequence encoding the TLR portion of the chimeric receptor can be derived from any TLR. Ten different human TLRs have been identified, cloned, and sequenced. TLRs are also known to exist in other mammals including, for example, mouse, rat, cow, pig, monkey and chimpanzee. The nucleic acid sequences of the ten human TLRs and many non-human TLRs are known and are readily accessible from various public sources, including Genbank and PCT Publication No. WO 01/90151. Similarly, the nucleic acid sequence encoding transmembrane and intracellular ITAM domains may be derived from any ITAM-containing molecule. The transmembrane and intracellular ITAM domains, however, need not be obtained from the same ITAM-containing molecule, nor does the transmembrane domain need to be obtained from an ITAM-containing molecule, so long as the desired structure and/or function of the chimeric receptor is retained. Preferably, the extracellular, transmembrane, and intracellular portions of the chimeric receptor are derived from mammalian sources, more preferably human sources.

Homologous sequences (both paralogues and orthologues) of the TLR and ITAM portions of the chimeric receptor can also be used so long as the desired structure and/or function of the chimeric receptor is retained. Methods for identifying homologous nucleic acid and amino acid sequences are well known in the art and include both hybridization-based and bioinformatics-based approaches (see Baxevanis and Ouellette, *Bioinformatics, A Practical Guide to the Analysis of Genes and Proteins* (2001). Nucleic acid sequences are preferred that hybridize under highly stringent conditions to the sequences described above, or their complements.

The nucleic acid sequences encoding the chimeric receptors can be produced using methods well known in the art, including chemical synthesis and PCR. Methods for producing fusion proteins are well known in the art, including PCR-based methods. For example, a first nucleic acid sequence encoding an extracellular domain of a TLR and a second nucleic acid sequence encoding the transmembrane and intracellular domains of a receptor comprising an intracellular ITAM can be separately amplified using PCR and then ligated together in frame in a vector. This can be facilitated by incorporation of compatible restriction sites onto the 3' end of the first nucleic acid sequences and the 5' end of the second nucleic acid sequence. This may require the addition or deletion of nucleotides (and the corresponding amino acids) not normally present or absent in the parent molecules, so long as the desired structure and/or activity is retained.

For proper expression in cells, nucleic acid sequences encoding the chimeric receptors will typically include nucleotides that encode an associated signal peptide. However, nucleic acid sequences lacking nucleotides that encode an associated signal peptide are also included within the scope of the invention. For example, a nucleic acid sequence encoding a chimeric receptor comprising the extracellular domain of TLR3 and the transmembrane and intracellular domains of a receptor comprising an intracellular ITAM can comprise the nucleotide sequence set forth in SEQ ID NO: 1 lacking the first 69-81 nucleotides. Similarly, a nucleic acid sequence encoding a chimeric receptor comprising the extracellular domain of TLR2 and the transmembrane and intracellular domains of a receptor comprising an intracellular ITAM can comprise the nucleotide sequence set forth in SEQ ID NO: 4 lacking the first 54-60 nucleotides. Again, due to the degeneracy of the genetic code, many different nucleotide sequences can encode the chimeric receptors comprising the amino acid sequences set forth in SEQ ID NOs: 2 and 4 lacking their associated signal peptides.

Insertion of a nucleic acid sequence encoding a chimeric receptor comprising the extracellular domain of a TLR and the transmembrane and intracellular domains of a receptor comprising an intracellular ITAM into a vector is easily accomplished when the 5' and 3' termini of the nucleic acid sequence and the vector comprise compatible restriction sites. If this cannot be done, it may be necessary to modify the termini of the nucleic acid and/or vector by digesting back single-stranded DNA overhangs generated by restriction endonuclease cleavage to produce blunt ends, or to achieve the same result by filling in the single-stranded termini with an appropriate DNA polymerase. Alternatively, desired sites may be produced, e.g., by ligating nucleotide sequences (linkers) onto the termini. Such linkers may comprise specific oligonucleotide sequences that define desired restriction sites. Restriction sites can also be generated by the use of PCR. The cleaved vector and DNA fragments may also be modified if required by homopolymeric tailing.

Recombinant expression vectors used in this invention are typically self-replicating DNA constructs comprising a nucleic acid sequence encoding a chimeric receptor comprising the extracellular domain of a TLR and the transmembrane and intracellular domains of a receptor comprising an intracellular ITAM operably linked to a suitable genetic control element that is capable of regulating expression of the nucleic acids in a compatible host cell. Genetic control elements may include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also may contain an origin of replication that allows the vector to replicate independently of the host cell.

Suitable prokaryotic promoters include the β-lactamase and lactose promoter systems, the tryptophan (trp) promoter system, the lambda $P_L$ promoter system and the tac promoter. Numerous expression vectors containing such control sequences are known in the art and available commercially. Suitable eukaryotic promoters include the cytomegalovirus (CMV) promoter, the SV40 early promoter region, the promoter contained in the 3' long terminal repeat of Rous sarcoma virus (RSV), the herpes TK promoter, the adenoviral promoter of an early or late (E1A, MLP, etc.) gene, the regulatory sequences of the metallothionein (MT) and phosphoglycerokinase (PGK) genes, as well as TLR promoters themselves. Inducible promoters and tissue specific promoters may also be used.

Suitable host cells for expressing a nucleic acid sequence encoding a chimeric receptor comprising the extracellular domain of a TLR and the transmembrane and intracellular domains of a receptor comprising an intracellular ITAM include prokaryotes and eukaryotes. Suitable prokaryotes include both gram negative and positive organisms, e.g., *E. coli* and *B. subtilis, S. typhimurium*, or any bacterial strain capable of expressing heterologous proteins. Suitable lower eukaryotes include yeast strains such *S. cerevisiae, S. pombe, Kluyveromyces* strains, *Candida*, or any yeast strain capable of expressing heterologous proteins. If the chimeric receptor is expressed in yeast or bacteria, it may be necessary to modify the protein produced therein, for example by phosphorylation or glycosylation of the appropriate sites, or by introduction of the targeting sequences, in order to obtain a functional protein.

The host cell is preferably a higher eukaryote cell line. Suitable higher eukaryote cell lines include both primary and established cell lines from animal cells, both of non-mammalian origin, e.g., insect cells and birds, and of mammalian origin, e.g., human, primates, and rodents.

Higher eukaryotic tissue culture cells are preferred hosts for the recombinant production of a chimeric receptor comprising the extracellular domain of a TLR and the transmembrane and intracellular domains of a receptor comprising an intracellular ITAM. Although any higher eukaryotic tissue culture cell line might be used, including insect baculovirus expression systems, mammalian cells are preferred. Suitable mammalian cell lines include HeLa cells, Chinese hamster ovary (CHO) cells, Syrian hamster kidney (HaK) cells, baby rat kidney (BRK) cells, baby hamster kidney (BHK) cells, mouse BaF3 cells, rat PC12 cells, African green monkey kidney (COS and CV-1) cells, human embryonic kidney (HEK 293) cells, A431 cells, Colo205 cells, 3T3 cells, mouse L cells, HL-60 cells, U937 cells, rat basophilic leukemia (RBL) cells and Jurkat cells. Preferably, the host cell is a mammalian cell capable of displaying calcium mobilization, such as U937 cells, RBL cells and Jurkat cells.

Because certain TLRs (e.g., TLR3, TLR7, TLR8, and TLR9) are normally localized in intracellular compartments of mammalian cells such as endosomes, it may be necessary to modify the extracellular TLR portion and/or add residues proximal to the linker region, close to the putative transmembrane domain, of the chimeric receptor for targeting to the cell surface. This may include, for example, alterations or substitution of the signal peptide or modification of the glycosylation sites, so long as the desired structure and/or function of the chimeric receptor is retained.

Methods for the transformation or transfection of mammalian cells are well known in the art and include electroporation, nucleofection, calcium phosphate co-precipitation, protoplast or spheroplast fusion, lipofection, DEAE-dextran-mediated transfection, biolistics, and viral infection. The transfected expression vector can be maintained transiently in the cell. Alternatively, if the expression vector contains a selectable marker, cells can be selected in which the vector has stably integrated into the genome by culturing the transfected cells in the appropriate antibiotic or drug. Sutiable dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin, and the bacterial xanthine-guanine phosphoribosyl transferase gene (also referred to as the gpt gene) which confers the ability to grow in the presence of mycophenolic acid.

Host cells expressing a chimeric receptor comprising the extracellular domain of a TLR and the transmembrane and intracellular domains of a receptor comprising an intracellular ITAM find utility in screening methods for identifying agonists of TLRs. As described below, the chimeric receptors display active ligand binding and trigger immediate calcium mobilization upon receptor activation, in contrast to the delayed cytokine or reporter response seen with wild-type TLRs. Calcium mobilization-based assays are distinct over assays that rely on delayed cytokine production or reporter induction, which suffer from an increased likelihood of cytotoxicity that can adversely affect the assays. The screening methods using the chimeric receptors are easily adaptable to high through-put screening procedures.

One embodiment of the agonist screening method involves (a) providing a host cell capable of displaying calcium mobilization comprising a recombinant vector comprising a chimeric receptor comprising the extracellular domain of a TLR and the transmembrane and intracellular domains of a receptor comprising an intracellular ITAM operably linked to a gene expression sequence; (b) culturing the host cell under conditions in which the recombinant nucleic acid molecule is expressed and the chimeric receptor is produced; (c) contacting the host cell with a candidate agent to be tested for TLR agonistic activity; and (d) measuring the level of calcium mobilization, whereby a TLR agonist is identified by measurement of an increased level of calcium mobilization compared to the level produced in the absence of such agonist. Changes in calcium mobilization can be measured using standard techniques, including fluorimetry (e.g., FLIPR®; Molecular Devices, Sunnyvale, Calif.) following cell loading with calcium indicator dyes, such as Indo-1 or Fluo-4, or calcium-dependent activation of aequorin bioluminescence.

The screening method can also be used to identify antagonists of TLRs. One embodiment of the antagonist screening method involves (a) providing a host cell capable of displaying calcium mobilization comprising a recombinant vector comprising a chimeric receptor comprising the extracellular domain of a TLR and the transmembrane and intracellular domains of a receptor comprising an intracellular ITAM operably linked to a gene expression sequence; (b) culturing the host cell under conditions in which the recombinant nucleic acid molecule is expressed and the chimeric receptor is produced; (c) contacting the host cell with a candidate agent to be tested for TLR antagonistic activity in the presence of a known TLR agonist; and (d) measuring the level of calcium mobilization, whereby a TLR antagonist is identified in the sample by measurement of a decreased level of calcium mobilization compared to the level produced in the presence of the known agonist alone. Known TLR agonists include natural ligands such as LPS, bacterial lipopeptides and lipoproteins, bacterial outer membrane proteins, lipoarabinomannan, glycosylphosphatidylinositol (GPI) anchors, taxol, zymosan, lipoteichoic acid, heat shock proteins (HSP) 60 and 70, fibrinogen, fibronectin, soluble heparin sulfate, hyaluronin, double stranded RNA, flagellin, pilin, single stranded viral, viral and bacterial unmethylated CpG DNA, chromatin-IgG complexes, and endogenous mRNA, as well as synthetic ligands such as R837, R848, CPG 7909, loxoribine, uridine, poly-IC, and poly-AU. The known agonist can also be one identified by the agonist screening method described above.

Generally, a plurality of assays can be run in parallel with different agent concentrations to obtain a differential response to the various concentrations. Typically, one of these concentrations serves as a negative control, i.e., at zero concentration or below the level of detection. Although the screening method generally is used as an assay to identify previously unknown molecules that can act as a therapeutic agent, the method can also be used to confirm and standardize the desired activity of a known TLR agonist or antagonist or to optimize the structure and/or activity of a known TLR agonist or antagonist during, e.g., rational drug design or molecular evolution procedures. In addition, the screening method can be performed at a range of pHs to identify, confirm, standardize, or optimize agonists or antagonists that are active in different cellular compartments. For example, the assay can be performed at a range of about pH 5.5 to about pH 7.5 to identify a physiologically active agonist or antagonist of TLR3, TLR7, TLR8, and TLR9, which are normally localized in endosomes.

Any candidate agent or compound can be screened in the above-described method. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to, peptides, saccharides, fatty acids, steroids, purines, pyrimidines, and various derivatives, structural analogs and combinations thereof. In particular, the screening method can be used to identify agonistic or antagonistic antibodies. Such antibodies include polyclonal, monoclonal, chimeric, humanized, single-chain and phage-displayed antibodies, and fragments thereof.

Candidate agents can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs.

In some embodiments of the screening methods, accessory molecules are co-expressed in the host cell for optimal cell surface expression and/or optimal recognition of ligands by the chimeric receptor. In one embodiment, the accessory molecule is one or more additional chimeric TLR receptors. For example, a chimeric TLR1 and/or TLR6 can be co-expressed with a chimeric TLR2 to provide optimal ligand recognition. In another embodiment, the accessory molecule is a non-TLR molecule. Examples of non-TLR accessory molecules include CD14, RP105, MD1, MD2, CD3, dectin-1, SR-A, LOX-1, LXR, MIP-2 receptor, SIGIRR, and A2R.

Diseases and conditions amenable to treatment with the identified TLR agonists and/or antagonists are those mediated by or influenced by TLR signaling and include the following:

(a) viral diseases such as, for example, diseases resulting from infection by an adenovirus, a herpesvirus (e.g., HSV-I, HSV-II, HHV-6, EBV, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenza virus), a paramyxovirus (e.g., parainfluenza virus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), a bunyavirus (e.g., hantavirus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella*;

(c) other infectious diseases, such as, for example, chlamydia, diseases resulting from infection of Mycoplasma, fungal diseases including, but not limited to, candidiasis, aspergillosis, histoplasmosis, cryptococcal meningitis, or parasitic diseases, including, but not limited to, malaria, Pneumocystis carinii and Pneumocystis jirovecii pneumonia, leishmaniasis, cryptosporidiosis, toxoplasmosis, and trypanosome infection;

(d) neoplastic diseases, such as, for example, intraepithelial neoplasias, cervical dysplasia, actinic keratosis, basal cell carcinoma, squamous cell carcinoma, renal cell carcinoma, Kaposi's sarcoma, melanoma, renal cell carcinoma, small cell and non-small cell lung cancer, adenocarcinoma including lung, breast, liver and prostate adenocarcinomas, leukemias, including, but not limited, to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $TH_2$-mediated, atopic diseases, such as, for example, atopic dermatitis or eczema, eosinophilia, asthma, allergy, allergic rhinitis, COPD, and Ommen's syndrome;

(f) certain autoimmune diseases such as, for example, systemic lupus erythematosus, essential thrombocythaemia, multiple sclerosis, discoid lupus, and alopecia areata;

(g) certain inflammatory conditions, such as, for example, rheumatoid arthritis, acne, ulcerative colitis, inflammatory bowel disease, Crohn's disease, systemic inflammatory response syndrome and cardiovascular disease, including, but not limited to, atherosclerosis and restenosis; and (h) diseases associated with wound repair such as, for example, inhibition of keloid formation and other types of scarring (e.g, enhancing wound healing, including chronic wounds).

For example, poly-IC, shown in the Examples below to activate chimeric TLR3/CD32a receptors, as well as poly-IC derivatives, such as poly(I)-poly($C_{12}U$) (Ampligen®, Hemispherx Biopharma, Philadelphia, Pa.) have been shown to have utility in the treatment of various viral-mediated diseases, such as Chronic Fatigue Syndrome (CFS), Acquired Immunodeficiency Syndrome (AIDS), Hepatitis B, coxsackie B3 virus-induced myocarditis, flavivirus-induced encephalitis, and genital herpes.

TLR agonists and/or antagonists identified by the above-described methods may also be used as adjuvants to improve vaccination strategies, including, but not limited to, anti-cancer vaccination.

Host cells expressing a chimeric receptor comprising the extracellular domain of a TLR and the transmembrane and intracellular domains of a receptor comprising an intracellular ITAM can also be used in assays to identify domains or residues important in TLR/ligand or TLR/accessory interactions or TLR dimerization through modification (either by mutagenesis or post-translational means) of the extracellular TLR domain. Changes in calcium mobilization following modification as compared to the unmodified chimeric receptor are indicative of an effect of the modification on one or more of these interactions. Modifications in the extracellular TLR domain can include changes in N- and O-linked glycosylation and disulfide bond formation, or any other change that affects the size, overall charge, structure, or function of the TLR domain, and can be introduced through substitutions, insertions, deletions, rearrangements, and the like using well-known site-directed and saturation mutagenesis techniques. Alternatively, the modifications can be introduced post-translationally using, e.g., glycosylation-blocking agents (e.g., tunicamycin, swainsonine) and deglycosylation enzymes (e.g., Endo-H, PNGase F, O-glycosidase, neuraminidase, etc.).

Specific embodiments according to the methods of the present invention will now be described in the following examples.

EXAMPLES

Example 1

Construction of Chimeric Human TLR3/CD32a and TLR2/CD32a Receptors

A nucleic acid sequence (SEQ ID NO: 1) encoding a mature human chimeric TLR3/CD32a receptor (SEQ ID NO: 2) comprising the extracellular domain of human TLR3 and the transmembrane and intracellular domains of human CD32a was prepared by PCR. The transmembrane domain of CD32a rather than TLR3 was chosen in order to favor cell surface expression. Briefly, the extracellular domain of human TLR3 was amplified by PCR on human TLR3 cDNA in pUNO (Invivogen, San Diego, Calif.) using the sense primer 5'-ACG CGT CGA CGA TCA TGA GAC AGA CTT TGC C-3' (SEQ ID NO: 5) and the antisense primer 5'-TAG CAT TAA TAG TTC AAA GGG GGC ACT GAC-3' (SEQ ID NO: 6) (based on Genbank Acc. No. NM_003265). The antisense primer was designed to add an additional leucine residue at the extracellular domain/transmembrane domain junction to create an AsnI restriction site. The 2385-bp fragment was gel purified and digested with SalI and AsnI. The intracellular and transmembrane domains of human CD32a were amplified by PCR on human PMBC DNA using the sense primer 5'-ATT AAT GGG GAT CAT TGT GGC-3' (SEQ ID NO: 7) and the antisense primer 5'-TAA TGC GGC CGC TGG CAT AAC GTT ACT CTT TAG-3' (SEQ ID NO: 8) (based on Genbank Acc. No. M31932). The 310-bp fragment was gel purified and digested with AsnI and NotI. The two fragments were ligated into the pMET7 expression vector (DNAX, Palo Alto, Calif.) digested with SalI and NotI to produce pTLR3/CD32a. Clones were selected by SalI/NotI digestion following plasmid miniprep. The construct was confirmed by DNA sequencing.

Similarly, a nucleic acid sequence (SEQ ID NO: 3) encoding a mature human chimeric TLR2/CD32a receptor (SEQ ID NO: 4) comprising the extracellular domain of human TLR2 and the transmembrane and intracellular domains of human CD32a was prepared by PCR. Briefly, the extracellular domain of human TLR2 was amplified by PCR on human TLR2 cDNA in PUNO (Invivogen) using the sense primer 5'-ACG CGT CGA CGA GCA TGC CAC ATA CTT TGT GGA TG -3' (SEQ ID NO: 9) and the antisense primer 5'-ATT AAT CTG TGA CAT TCC GAG ACC G-3' (SEQ ID NO: 10) (based on Genbank Acc. No. NM_003264). The antisense primer was designed to add an additional leucine residue at the extracellular domain/transmembrane domain junction to create a AsnI restriction site. The 2114-bp fragment was gel purified and digested with SalI and AsnI. The intracellular and transmembrane domains of human CD32a were amplified by PCR on human PMBC DNA using the sense primer 5'-ATT AAT GGG GAT CAT TGT GGC-3' (SEQ ID NO: 7) and the antisense primer 5'-TAA TGC GGC CGC TGG CAT AAC GTT ACT CTT TAG-3' (SEQ ID NO: 8) (based on Genbank Acc. No. M31932). The 310-bp fragment was gel purified and digested with AsnI and NotI. The two fragments were ligated into the pMET7 expression vector (DNAX, Palo Alto, Calif.) digested with SalI and NotI (pTLR2/CD32a). Clones were selected by SalI/NotI digestion following plasmid miniprep. The construct was confirmed by DNA sequencing.

Example 2

Transient Expression and Activation of Chimeric Human TLR3/CD32a and TLR2/CD32a Receptors The pTLR3/CD32a and pTLR2/CD32a expression vectors were transfected into HEK 293 cells. Cell surface expression of the chimeric receptors was detected using anti-TLR3 and anti-TLR2 antibodies, while no signal was detected on untransfected cells.

The hematopoietic cell line U937 was used for further biological investigation because of the ability of this cell line to display calcium mobilization upon cross-linking of endogenous CD32a using anti-CD32a antibodies followed by secondary antibody (as detected by fluorimetry following loading of the cells with Indo-1 or Fluo-4). Thus, U937 cells express all of the cellular components required for calcium mobilization mediated through CD32a activation.

Transient transfection of the pTLR3/CD32a and pTLR2/CD32a expression vectors into U937 allowed high level cell surface expression of the chimeric molecule as detected with anti-TLR3 or anti-TLR2 antibodies, while no expression was observed on untransfected cells or cells transfected with the other chimeric vector. Anti-TLR antibodies followed by secondary antibodies to cross-link the chimeric receptors induced a potent calcium mobilization. In contrast, no calcium mobilization was observed upon treatment with anti-TLR antibodies alone, indicating that TLR multimerization is required for signaling through CD32a.

Poly-IC, a synthetic double-stranded RNA ligand for TLR3, was then tested for its ability to stimulate the chimeric TLR3/CD32a receptor. Poly(I) (15, 30 and 40 mers) and poly(C) (15, 30 and 40 mers) (Ambion, Huntingdon, Cambridgeshire, U.K. and Invitrogen, Cergy Pontoise, France respectively) were annealed in equal proportions according to their size for 15 minutes at 95° C. Independently, fragmentation of high molecular weight poly-IC (>5000 bp) was performed by metal-induced hydrolysis as recommended by Affymetrix (High Wycombe, UK). Briefly, 200 μg poly-IC was incubated with 40 μl of 5×RNA fragmentation buffer (200 mM Tris-acetate, pH 8.1, 500 mM KOAc, 150 mM MgOAc) in a final volume of 200 μl, for 35 min at 900° C. Fragmented poly-IC (100-200 bp) was then allowed to reach room temperature before purification. The relative sizes of dsRNA fragments were examined by electrophoresis in 2% agarose gel.

When poly-IC was used to bind to the chimeric TLR3/CD32a receptor, an immediate calcium mobilization of similar intensity to that induced by anti-TLR antibodies was observed. Similar results were obtained with poly-AU, another synthetic TLR3 ligand. In contrast, no calcium mobilization was observed with untransfected cells or cells transfected with pTLR2/CD32a upon treatment with poly-IC. Longer fragments of poly-IC triggered calcium fluxes of greater intensity than small fragments, suggesting that potency is proportional to the ability of fragments to mediate TLR3 multimerization. Sequential stimulation with an optimal concentration of poly-IC resulted in desensitization to a second stimulation to either poly-IC or to anti-TLR3-mediated cross-linking, again indicating that TLR multimerization is required for signaling through CD32a. Dose response to poly-IC showed that a lower dose of poly-IC was required to detect biological response in this assay (0.025 μg/ml) compared to cytokine induction in PBMC (2.5 μg/ml).

Example 3

Stable Expression and Activation of Chimeric Human TLR3/CD32a Receptor

U937 cells were stably transfected with pTLR3/CD32a using co-transfection with an antibiotic-encoding plasmid and antibiotic selection followed by limiting dilution cloning. Clones were selected based on their cell surface expression level of TLR3. Clones exhibiting cell surface expression of the chimeric receptor exhibited robust calcium mobilization upon treatment with poly-IC or cross-linking anti-TLR3 antibodies. These clones expand very easily (up to $10^9$ cells) and can be maintained for several months in culture without losing the expression of the chimeric receptor. Using these clones, dose response to poly-IC showed an even higher sensitivity to poly-IC (10-30 ng/ml) than seen with the transiently transfected cells. Such stable clones provide a useful method for high through-put screening of candidate agents for the identification of TLR agonists and antagonists.

Example 4

Role of Glycosylation in Ligand Recognition by TLR3

In order to determine the role of glycosylation in ligand recognition by TLR3, a chimeric TLR3/CD32a receptor lacking two N-glycosylation sites (N196 and N247 as numbered at Genbank Acc. No. NP_003256) was generated by site-directed mutagenesis and co-transfected into HEK 293 cells with a reporter plasmid containing concensus NFκB sites which, when activated, directs the expression of firefly luciferase. The mutant TLR3 molecules were expressed in a similar fashion to the native TLR3 molecules as determined by Western blotting (albeit with a smaller molecular weight), yet were completely inactive with poly-IC, showing that glycosylation is important in mediating poly-IC binding to TLR3.

Example 5

Interaction Between Chimeric Human TLR3/CD32a Receptor and Poly-IC is Dependent on pH Wild type TLR3 has previously been described as an intracellular receptor, at least in dendritic cells (DC), and interaction with its ligand occurs in early endosomes. These intracellular compartments display an acidic pH that has been shown to play a key role in the interaction between, e.g., TLR9 and CpG. U937 cells expressing the chimeric human TLR3/CD32a receptor at the cell surface were used to investigate the effect of the extracellular pH on poly-IC-mediated calcium mobilization. Administration of poly-IC to the cells at a range of pHs from 5.5-7.5 indicated that 6.5 acidic pH was required for optimal response to poly-IC, while a pH of 7.2 and greater prevented biological response. In contrast, the pH had no influence on calcium mobilization mediated by cross-linking anti-TLR3 antibodies, indicating that the chimeric receptor was properly reaching the cell surface. These results show that pH has a strong impact on the interaction between poly-IC and TLR3 and provide a basis for identifying agonists and antagonists that are physiologically active in various cellular compartments, such as endosomes.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims. For example, while the invention has been described with reference to TLRs, other embodiments include the recombinant coupling of an intracellular ITAM-containing molecule to any receptor (both intracellular and cell surface) that can be directed to the cell surface and for which ligand interaction causes multimerization.

What is claimed:

1. A chimeric receptor comprising the extracellular ligand-binding domain of a toll-like receptor (TLR) and the transmembrane and intracellular domains of a receptor comprising an intracellular ITAM, wherein said ITAM comprises the amino acid sequence of any one of SEQ ID NOS: 11-13, wherein binding of a ligand of said TLR to said chimeric receptor results in calcium mobilization.

2. The chimeric receptor of claim 1, wherein the TLR is TLR3 and wherein the ligand is double stranded RNA or endogenous mRNA.

3. The chimeric receptor of claim 2, wherein the receptor comprising an intracellular ITAM is CD32a.

4. The chimeric receptor of claim 3 comprising the amino acid sequence set forth in SEQ ID NO: 2.

5. A chimeric receptor comprising the amino acid sequence set forth in SEQ ID NO: 2 without the associated signal peptide sequence.

6. The chimeric receptor of claim 1, wherein the TLR is TLR2 and wherein said ligand is a bacterial lipoprotein or lipoteichoic acid.

7. The chimeric receptor of claim 6, wherein the receptor comprising an intracellular ITAM is CD32a.

8. The chimeric receptor of claim 7 comprising the amino acid sequence set forth in SEQ ID NO: 4.

9. A chimeric receptor comprising the amino acid sequence set forth in SEQ ID NO: 4 without the associated signal peptide sequence.

* * * * *

SEQUENCE LISTING

<160> NUMBER OF SEQ ID NOS: 13

<210> SEQ ID NO 1
<211> LENGTH: 2424
<212> TYPE: DNA
<213> ORGANISM: Artificial Sequence
<220> FEATURE:
<223> OTHER INFORMATION: Description of Artificial Sequence: Synthetic
      TLR3/CD32a fusion polynucleotide

<400> SEQUENCE: 1

```
atgagacaga ctttgccttg tatctacttt tgggggggcc ttttgccctt tgggatgctg      60
tgtgcatcct ccaccaccaa gtgcactgtt agccatgaag ttgctgactg cagccacctg     120
aagttgactc aggtacccga tgatctaccc acaaacataa cagtgttgaa ccttacccat     180
aatcaactca gaagattacc agccgccaac ttcacaaggt atagccagct aactagcttg     240
gatgtaggat taacaccat ctcaaaactg gagccagaat tgtgccagaa acttcccatg      300
ttaaaagttt tgaacctcca gcacaatgag ctatctcaac tttctgataa aacctttgcc     360
ttctgcacga atttgactga actccatctc atgtccaact caatccagaa aattaaaat      420 aatcccttg tcaagcagaa gaatttaatc acattagatc tgtctcataa tggcttgtca      480
tctacaaaat taggaactca ggttcagctg gaaaatctcc aagagcttct attatcaaac     540
aataaaattc aagcgctaaa aagtgaagaa ctggatatct ttgccaattc atcttaaaa      600 aaattagagt tgtcatcgaa tcaaattaaa gagttttctc cagggtgttt tcacgcaatt     660
ggaagattat ttggcctctt tctgaacaat gtccagctgg gtcccagcct tacagagaag     720
ctatgtttgg aattagcaaa cacaagcatt cggaatctgt ctctgagtaa cagccagctg     780
tccaccacca gcaatacaac tttcttggga ctaaagtgga caaatctcac tatgctcgat     840
ctttcctaca caaacttaaa tgtggttggt aacgattcct ttgcttggct tccacaacta     900
gaatatttct tcctagagta taataatata cagcatttgt tttctcactc tttgcacggg     960
cttttcaatg tgaggtacct gaatttgaaa cggtctttta ctaaacaaag tatttccctt    1020
gcctcactcc ccaagattga tgatttttct tttcagtggc taaaatgttt ggagcacctt    1080
aacatggaag ataatgatat tccaggcata aaaagcaata tgttcacagg attgataaac    1140
ctgaaatact taagtctatc caactccttt acaagtttgc gaactttgac aaatgaaaca    1200
tttgtatcac ttgctcattc tcccttacac atactcaacc taaccaagaa taaaatctca    1260
aaaatagaga gtgatgcttt ctcttggttg ggccacctag aagtacttga cctgggcctt    1320
aatgaaattg gcaagaact cacaggccag gaatggagag tctagaaaa tatttttgaa     1380 atctatcttt cctacaacaa gtacctgcag ctgactagga actcctttgc cttggtccca    1440
```

```
agccttcaac gactgatgct ccgaagggtg gcccttaaaa atgtggatag ctctccttca   1500
ccattccagc ctcttcgtaa cttgaccatt ctggatctaa gcaacaacaa catagccaac   1560
ataaatgatg acatgttgga gggtcttgag aaactagaaa ttctcgattt gcagcataac   1620
aacttagcac ggctctggaa acacgcaaac cctggtggtc ccatttattt cctaaagggt   1680
ctgtctcacc tccacatcct taacttggag tccaacggct ttgacgagat cccagttgag   1740
gtcttcaagg atttatttga actaaagatc atcgatttag gattgaataa tttaaacaca   1800
cttccagcat ctgtctttaa taatcaggtg tctctaaagt cattgaacct tcagaagaat   1860
ctcataacat ccgttgagaa gaaggttttc gggccagctt tcaggaacct gactgagtta   1920
gatatgcgct ttaatccctt tgattgcacg tgtgaaagta ttgcctggtt tgttaattgg   1980
attaacgaga cccataccaa catccctgag ctgtcaagcc actacctttg caacactcca   2040
cctcactatc atgggttccc agtgagactt tttgatacat catcttgcaa agacagtgcc   2100
ccctttgaac tattaatggg gatcattgtg gctgtggtca ttgcgactgc tgtagcagcc   2160
attgttgctg ctgtagtggc cttgatctac tgcaggaaaa agcggatttc agccaattcc   2220
actgatcctg tgaaggctgc ccaatttgag ccacctggac gtcaaatgat tgccatcaga   2280
aagagacaac ttgaagaaac caacaatgac tatgaaacag ctgacggcgg ctacatgact   2340
ctgaacccta gggcacctac tgacgatgat aaaaacatct acctgactct tcctcccaac   2400
gaccatgtca acagtaataa ctaa                                         2424

<210> SEQ ID NO 2
<211> LENGTH: 807
<212> TYPE: PRT
<213> ORGANISM: Artificial Sequence
<220> FEATURE:
<223> OTHER INFORMATION: Description of Artificial Sequence: Synthetic
      TLR3/CD32a fusion polypeptide

<400> SEQUENCE: 2

Met Arg Gln Thr Leu Pro Cys Ile Tyr Phe Trp Gly Gly Leu Leu Pro
1               5                   10                  15

Phe Gly Met Leu Cys Ala Ser Ser Thr Thr Lys Cys Thr Val Ser His
            20                  25                  30

Glu Val Ala Asp Cys Ser His Leu Lys Leu Thr Gln Val Pro Asp Asp
        35                  40                  45

Leu Pro Thr Asn Ile Thr Val Leu Asn Leu Thr His Asn Gln Leu Arg
    50                  55                  60

Arg Leu Pro Ala Ala Asn Phe Thr Arg Tyr Ser Gln Leu Thr Ser Leu
65                  70                  75                  80

Asp Val Gly Phe Asn Thr Ile Ser Lys Leu Glu Pro Glu Leu Cys Gln
                85                  90                  95

Lys Leu Pro Met Leu Lys Val Leu Asn Leu Gln His Asn Glu Leu Ser
            100                 105                 110

Gln Leu Ser Asp Lys Thr Phe Ala Phe Cys Thr Asn Leu Thr Glu Leu
        115                 120                 125

His Leu Met Ser Asn Ser Ile Gln Lys Ile Lys Asn Asn Pro Phe Val
    130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
```

-continued

```
            180                 185                 190
Ile Phe Ala Asn Ser Ser Leu Lys Lys Leu Glu Leu Ser Ser Asn Gln
            195                 200                 205
Ile Lys Glu Phe Ser Pro Gly Cys Phe His Ala Ile Gly Arg Leu Phe
        210                 215                 220
Gly Leu Phe Leu Asn Asn Val Gln Leu Gly Pro Ser Leu Thr Glu Lys
225                 230                 235                 240
Leu Cys Leu Glu Leu Ala Asn Thr Ser Ile Arg Asn Leu Ser Leu Ser
                245                 250                 255
Asn Ser Gln Leu Ser Thr Thr Ser Asn Thr Thr Phe Leu Gly Leu Lys
            260                 265                 270
Trp Thr Asn Leu Thr Met Leu Asp Leu Ser Tyr Asn Asn Leu Asn Val
        275                 280                 285
Val Gly Asn Asp Ser Phe Ala Trp Leu Pro Gln Leu Glu Tyr Phe Phe
    290                 295                 300
Leu Glu Tyr Asn Asn Ile Gln His Leu Phe Ser His Ser Leu His Gly
305                 310                 315                 320
Leu Phe Asn Val Arg Tyr Leu Asn Leu Lys Arg Ser Phe Thr Lys Gln
                325                 330                 335
Ser Ile Ser Leu Ala Ser Leu Pro Lys Ile Asp Asp Phe Ser Phe Gln
            340                 345                 350
Trp Leu Lys Cys Leu Glu His Leu Asn Met Glu Asp Asn Asp Ile Pro
        355                 360                 365
Gly Ile Lys Ser Asn Met Phe Thr Gly Leu Ile Asn Leu Lys Tyr Leu
    370                 375                 380
Ser Leu Ser Asn Ser Phe Thr Ser Leu Arg Thr Leu Thr Asn Glu Thr
385                 390                 395                 400
Phe Val Ser Leu Ala His Ser Pro Leu His Ile Leu Asn Leu Thr Lys
                405                 410                 415
Asn Lys Ile Ser Lys Ile Glu Ser Asp Ala Phe Ser Trp Leu Gly His
            420                 425                 430
Leu Glu Val Leu Asp Leu Gly Leu Asn Glu Ile Gly Gln Glu Leu Thr
        435                 440                 445
Gly Gln Glu Trp Arg Gly Leu Glu Asn Ile Phe Glu Ile Tyr Leu Ser
    450                 455                 460
Tyr Asn Lys Tyr Leu Gln Leu Thr Arg Asn Ser Phe Ala Leu Val Pro
465                 470                 475                 480
Ser Leu Gln Arg Leu Met Leu Arg Arg Val Ala Leu Lys Asn Val Asp
                485                 490                 495
Ser Ser Pro Ser Pro Phe Gln Pro Leu Arg Asn Leu Thr Ile Leu Asp
            500                 505                 510
Leu Ser Asn Asn Asn Ile Ala Asn Ile Asn Asp Asp Met Leu Glu Gly
        515                 520                 525
Leu Glu Lys Leu Glu Ile Leu Asp Leu Gln His Asn Asn Leu Ala Arg
    530                 535                 540
Leu Trp Lys His Ala Asn Pro Gly Gly Pro Ile Tyr Phe Leu Lys Gly
545                 550                 555                 560
Leu Ser His Leu His Ile Leu Asn Leu Glu Ser Asn Gly Phe Asp Glu
                565                 570                 575
Ile Pro Val Glu Val Phe Lys Asp Leu Phe Glu Leu Lys Ile Ile Asp
            580                 585                 590
Leu Gly Leu Asn Asn Leu Asn Thr Leu Pro Ala Ser Val Phe Asn Asn
        595                 600                 605
```

-continued

```
Gln Val Ser Leu Lys Ser Leu Asn Leu Gln Lys Asn Leu Ile Thr Ser
        610                 615                 620

Val Glu Lys Lys Val Phe Gly Pro Ala Phe Arg Asn Leu Thr Glu Leu
625                 630                 635                 640

Asp Met Arg Phe Asn Pro Phe Asp Cys Thr Cys Glu Ser Ile Ala Trp
                645                 650                 655

Phe Val Asn Trp Ile Asn Glu Thr His Thr Asn Ile Pro Glu Leu Ser
            660                 665                 670

Ser His Tyr Leu Cys Asn Thr Pro His Tyr His Gly Phe Pro Val
        675                 680                 685

Arg Leu Phe Asp Thr Ser Ser Cys Lys Asp Ser Ala Pro Phe Glu Leu
    690                 695                 700

Leu Met Gly Ile Ile Val Ala Val Val Ile Ala Thr Ala Val Ala Ala
705                 710                 715                 720

Ile Val Ala Ala Val Val Ala Leu Ile Tyr Cys Arg Lys Lys Arg Ile
                725                 730                 735

Ser Ala Asn Ser Thr Asp Pro Val Lys Ala Ala Gln Phe Glu Pro Pro
            740                 745                 750

Gly Arg Gln Met Ile Ala Ile Arg Lys Arg Gln Leu Glu Glu Thr Asn
        755                 760                 765

Asn Asp Tyr Glu Thr Ala Asp Gly Gly Tyr Met Thr Leu Asn Pro Arg
    770                 775                 780

Ala Pro Thr Asp Asp Asp Lys Asn Ile Tyr Leu Thr Leu Pro Pro Asn
785                 790                 795                 800

Asp His Val Asn Ser Asn Asn
                805
```

<210> SEQ ID NO 3
<211> LENGTH: 2067
<212> TYPE: DNA
<213> ORGANISM: Artificial Sequence
<220> FEATURE:
<223> OTHER INFORMATION: Description of Artificial Sequence: Synthetic
    TLR2/CD32a fusion polynucleotide

<400> SEQUENCE: 3

```
atgccacata ctttgtggat ggtgtgggtc ttgggggtca tcatcagcct ctccaaggaa     60
gaatcctcca atcaggcttc tctgtcttgt daccgcaatg gtatctgcaa gggcagctca    120
ggatctttaa actccattcc ctcagggctc acagaagctg taaaaagcct tgacctgtcc    180
aacaacagga tcacctacat tagcaacagt gacctacaga ggtgtgtgaa cctccaggct    240
ctggtgctga catccaatgg aattaacaca atagaggaag attctttttc ttccctgggc    300
agtcttgaac atttagactt atcctataat tacttatcta atttatcgtc ttcctggttc    360
aagccccttt cttctttaac attcttaaac ttactgggaa atcctacaa acccctaggg    420 gaaacatctc ttttttctca tctcacaaaa ttgcaaatcc tgagagtggg aaatatggac    480
accttcacta agattcaaag aaaagatttt gctggactta ccttccttga ggaacttgag    540
attgatgctt cagatctaca gagctatgag ccaaaaagtt tgaagtcaat tcagaatgta    600
agtcatctga tccttcatat gaagcagcat attttactgc tggagatttt tgtagatgtt    660
acaagttccg tggaatgttt ggaactgcga gatactgatt ggacactttt ccattttttca   720 gaactatcca ctggtgaaac aaattcattg attaaaaagt ttacatttag aaatgtgaaa    780
atcaccgatg aaagtttgtt tcaggttatg aaactttgga atcagatttc tggattgtta    840
```

-continued

```
gaattagagt tgatgactg taccccttaat ggagttggta attttagagc atctgataat    900
gacagagtta tagatccagg taaagtggaa acgttaacaa tccggaggct gcatattcca    960
aggttttact tattttatga tctgagcact ttatattcac ttacagaaag agttaaaaga   1020
atcacagtag aaaacagtaa agttttctg gttccttgtt tactttcaca acatttaaaa   1080
tcattagaat acttggatct cagtgaaaat ttgatggttg aagaatactt gaaaaattca   1140
gcctgtgagg atgcctggcc ctctctacaa actttaattt taaggcaaaa tcatttggca   1200
tcattggaaa aaaccggaga ctttgctc actctgaaaa acttgactaa cattgatatc   1260
agtaagaata gttttcattc tatgcctgaa acttgtcagt ggccagaaaa gatgaaatat   1320
ttgaacttat ccagcacacg aatacacagt gtaacaggct gcattcccaa gacactggaa   1380
attttagatg ttagcaacaa caatctcaat ttatttctt tgaatttgcc gcaactcaaa   1440
gaactttata tttccagaaa taagttgatg actctaccag atgcctccct cttacccatg   1500
ttactagtat tgaaaatcag taggaatgca ataactacgt tttctaagga gcaacttgac   1560
tcatttcaca cactgaagac tttggaagct ggtggcaata acttcatttg ctcctgtgaa   1620
ttcctctcct tcactcagga gcagcaagca ctggccaaag tcttgattga ttggccagca   1680
aattacctgt gtgactctcc atcccatgtg cgtggccagc aggttcagga tgtccgcctc   1740
tcggaatgtc acagattaat ggggatcatt gtggctgtgg tcattgcgac tgctgtagca   1800
gccattgttg ctgctgtagt ggccttgatc tactgcagga aaaagcggat ttcagccaat   1860
tccactgatc ctgtgaaggc tgcccaattt gagccacctg acgtcaaat gattgccatc   1920
agaaagagac aacttgaaga aaccaacaat gactatgaaa cagctgacgg cggctacatg   1980
actctgaacc ctagggcacc tactgacgat gataaaaaca tctacctgac tcttcctccc   2040
aacgaccatg tcaacagtaa taactaa                                      2067
```

<210> SEQ ID NO 4
<211> LENGTH: 688
<212> TYPE: PRT
<213> ORGANISM: Artificial Sequence
<220> FEATURE:
<223> OTHER INFORMATION: Description of Artificial Sequence: Synthetic TLR2/CD32a fusion polypeptide

<400> SEQUENCE: 4

```
Met Pro His Thr Leu Trp Met Val Trp Val Leu Gly Val Ile Ile Ser
1               5                   10                  15

Leu Ser Lys Glu Glu Ser Ser Asn Gln Ala Ser Leu Ser Cys Asp Arg
            20                  25                  30

Asn Gly Ile Cys Lys Gly Ser Ser Gly Ser Leu Asn Ser Ile Pro Ser
        35                  40                  45

Gly Leu Thr Glu Ala Val Lys Ser Leu Asp Leu Ser Asn Asn Arg Ile
    50                  55                  60

Thr Tyr Ile Ser Asn Ser Asp Leu Gln Arg Cys Val Asn Leu Gln Ala
65                  70                  75                  80

Leu Val Leu Thr Ser Asn Gly Ile Asn Thr Ile Glu Glu Asp Ser Phe
                85                  90                  95

Ser Ser Leu Gly Ser Leu Glu His Leu Asp Leu Ser Tyr Asn Tyr Leu
            100                 105                 110

Ser Asn Leu Ser Ser Ser Trp Phe Lys Pro Leu Ser Ser Leu Thr Phe
        115                 120                 125

Leu Asn Leu Leu Gly Asn Pro Tyr Lys Thr Leu Gly Glu Thr Ser Leu
    130                 135                 140
```

```
Phe Ser His Leu Thr Lys Leu Gln Ile Leu Arg Val Gly Asn Met Asp
145                 150                 155                 160

Thr Phe Thr Lys Ile Gln Arg Lys Asp Phe Ala Gly Leu Thr Phe Leu
                165                 170                 175

Glu Glu Leu Glu Ile Asp Ala Ser Asp Leu Gln Ser Tyr Glu Pro Lys
            180                 185                 190

Ser Leu Lys Ser Ile Gln Asn Val Ser His Leu Ile Leu His Met Lys
        195                 200                 205

Gln His Ile Leu Leu Leu Glu Ile Phe Val Asp Val Thr Ser Ser Val
    210                 215                 220

Glu Cys Leu Glu Leu Arg Asp Thr Asp Leu Asp Thr Phe His Phe Ser
225                 230                 235                 240

Glu Leu Ser Thr Gly Glu Thr Asn Ser Leu Ile Lys Lys Phe Thr Phe
                245                 250                 255

Arg Asn Val Lys Ile Thr Asp Glu Ser Leu Phe Gln Val Met Lys Leu
                260                 265                 270

Leu Asn Gln Ile Ser Gly Leu Leu Glu Leu Glu Phe Asp Asp Cys Thr
            275                 280                 285

Leu Asn Gly Val Gly Asn Phe Arg Ala Ser Asp Asn Asp Arg Val Ile
        290                 295                 300

Asp Pro Gly Lys Val Glu Thr Leu Thr Ile Arg Arg Leu His Ile Pro
305                 310                 315                 320

Arg Phe Tyr Leu Phe Tyr Asp Leu Ser Thr Leu Tyr Ser Leu Thr Glu
                325                 330                 335

Arg Val Lys Arg Ile Thr Val Glu Asn Ser Lys Val Phe Leu Val Pro
                340                 345                 350

Cys Leu Leu Ser Gln His Leu Lys Ser Leu Glu Tyr Leu Asp Leu Ser
            355                 360                 365

Glu Asn Leu Met Val Glu Glu Tyr Leu Lys Asn Ser Ala Cys Glu Asp
        370                 375                 380

Ala Trp Pro Ser Leu Gln Thr Leu Ile Leu Arg Gln Asn His Leu Ala
385                 390                 395                 400

Ser Leu Glu Lys Thr Gly Glu Thr Leu Leu Thr Leu Lys Asn Leu Thr
                405                 410                 415

Asn Ile Asp Ile Ser Lys Asn Ser Phe His Ser Met Pro Glu Thr Cys
                420                 425                 430

Gln Trp Pro Glu Lys Met Lys Tyr Leu Asn Leu Ser Ser Thr Arg Ile
            435                 440                 445

His Ser Val Thr Gly Cys Ile Pro Lys Thr Leu Glu Ile Leu Asp Val
        450                 455                 460

Ser Asn Asn Asn Leu Asn Leu Phe Ser Leu Asn Leu Pro Gln Leu Lys
465                 470                 475                 480

Glu Leu Tyr Ile Ser Arg Asn Lys Leu Met Thr Leu Pro Asp Ala Ser
                485                 490                 495

Leu Leu Pro Met Leu Leu Val Leu Lys Ile Ser Arg Asn Ala Ile Thr
            500                 505                 510

Thr Phe Ser Lys Glu Gln Leu Asp Ser Phe His Thr Leu Lys Thr Leu
        515                 520                 525

Glu Ala Gly Gly Asn Asn Phe Ile Cys Ser Cys Glu Phe Leu Ser Phe
    530                 535                 540

Thr Gln Glu Gln Gln Ala Leu Ala Lys Val Leu Ile Asp Trp Pro Ala
545                 550                 555                 560
```

-continued

```
Asn Tyr Leu Cys Asp Ser Pro Ser His Val Arg Gly Gln Gln Val Gln
                565                 570                 575

Asp Val Arg Leu Ser Glu Cys His Arg Leu Met Gly Ile Ile Val Ala
            580                 585                 590

Val Val Ile Ala Thr Ala Val Ala Ile Val Ala Ala Val Val Ala
        595                 600                 605

Leu Ile Tyr Cys Arg Lys Lys Arg Ile Ser Ala Asn Ser Thr Asp Pro
    610                 615                 620

Val Lys Ala Ala Gln Phe Glu Pro Pro Gly Arg Gln Met Ile Ala Ile
625                 630                 635                 640

Arg Lys Arg Gln Leu Glu Glu Thr Asn Asn Asp Tyr Glu Thr Ala Asp
                645                 650                 655

Gly Gly Tyr Met Thr Leu Asn Pro Arg Ala Pro Thr Asp Asp Asp Lys
            660                 665                 670

Asn Ile Tyr Leu Thr Leu Pro Pro Asn Asp His Val Asn Ser Asn Asn
        675                 680                 685

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      PCR sense primer

<400> SEQUENCE: 5
acgcgtcgac gatcatgaga cagactttgc c                                 31

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      PCR antisense primer

<400> SEQUENCE: 6
tagcattaat agttcaaagg gggcactgac                                   30

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      PCR sense primer

<400> SEQUENCE: 7
attaatgggg atcattgtgg c                                            21

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      PCR antisense primer

<400> SEQUENCE: 8
taatgcggcc gctggcataa cgttactctt tag                               33

<210> SEQ ID NO 9
<211> LENGTH: 35
```

```
<212> TYPE: DNA
<213> ORGANISM: Artificial Sequence
<220> FEATURE:
<223> OTHER INFORMATION: Description of Artificial Sequence: Synthetic
      PCR sense primer

<400> SEQUENCE: 9
acgcgtcgac gagcatgcca catactttgt ggatg                               35

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      PCR antisense primer

<400> SEQUENCE: 10
attaatctgt gacattccga gaccg                                         25

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      ITAM consensus sequence
<220> FEATURE:
<221> NAME/KEY: MOD_RES
<222> LOCATION: (1)..(1)
<223> OTHER INFORMATION: Glu or Asp
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (7)..(7)
<223> OTHER INFORMATION: Leu or Ile
<220> FEATURE:
<221> NAME/KEY: MOD_RES
<222> LOCATION: (8)..(13)
<223> OTHER INFORMATION: Any amino acid
<220> FEATURE:
<221> NAME/KEY: MOD_RES
<222> LOCATION: (15)..(16)
<223> OTHER INFORMATION: Any amino acid
<220> FEATURE:
<221> NAME/KEY: MOD_RES
<222> LOCATION: (17)..(17)
<223> OTHER INFORMATION: Leu or Ile

<400> SEQUENCE: 11

Xaa Xaa Xaa Tyr Xaa Xaa Xaa Xaa Xaa Xaa Xaa Xaa Xaa Tyr Xaa Xaa
1               5                   10                  15

Xaa

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      ITAM consensus sequence
<220> FEATURE:
<221> NAME/KEY: MOD_RES
<222> LOCATION: (1)..(1)
<223> OTHER INFORMATION: Glu or Asp
```

```
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (7)..(7)
<223> OTHER INFORMATION: Leu or Ile
<220> FEATURE:
<221> NAME/KEY: MOD_RES
<222> LOCATION: (8)..(14)
<223> OTHER INFORMATION: Any amino acid
<220> FEATURE:
<221> NAME/KEY: MOD_RES
<222> LOCATION: (16)..(17)
<223> OTHER INFORMATION: Any amino acid
<220> FEATURE:
<221> NAME/KEY: MOD_RES
<222> LOCATION: (18)..(18)
<223> OTHER INFORMATION: Leu or Ile

<400> SEQUENCE: 12

Xaa Xaa Xaa Tyr Xaa Xaa Xaa Xaa Xaa Xaa Xaa Xaa Xaa Xaa Tyr Xaa
1               5                   10                  15

Xaa Xaa

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic
      ITAM consensus sequence
<220> FEATURE:
<221> NAME/KEY: MOD_RES
<222> LOCATION: (1)..(1)
<223> OTHER INFORMATION: Glu or Asp
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (7)..(7)
<223> OTHER INFORMATION: Leu or Ile
<220> FEATURE:
<221> NAME/KEY: MOD_RES
<222> LOCATION: (8)..(15)
<223> OTHER INFORMATION: Any amino acid
<220> FEATURE:
<221> NAME/KEY: MOD_RES
<222> LOCATION: (17)..(18)
<223> OTHER INFORMATION: Any amino acid
<220> FEATURE:
<221> NAME/KEY: MOD_RES
<222> LOCATION: (19)..(19)
<223> OTHER INFORMATION: Leu or Ile

<400> SEQUENCE: 13

Xaa Xaa Xaa Tyr Xaa Xaa Xaa Xaa Xaa Xaa Xaa Xaa Xaa Xaa Xaa Tyr
1               5                   10                  15

Xaa Xaa Xaa
```